United States Patent
Saab

(10) Patent No.: US 7,524,321 B2
(45) Date of Patent: *Apr. 28, 2009

(54) MULTI-LUMEN CATHETERS AND METHODS FOR USING SAME

(76) Inventor: Mark A. Saab, 396 Andover St., Lowell, MA (US) 01852

( * ) Notice: Subject to any disclaimer, the term of this patent is extended or adjusted under 35 U.S.C. 154(b) by 89 days.

This patent is subject to a terminal disclaimer.

(21) Appl. No.: 11/282,329

(22) Filed: Nov. 18, 2005

(65) Prior Publication Data

US 2006/0106336 A1   May 18, 2006

Related U.S. Application Data

(60) Division of application No. 10/259,117, filed on Sep. 27, 2002, now Pat. No. 6,966,889, which is a continuation-in-part of application No. 10/011,137, filed on Dec. 7, 2001, now Pat. No. 6,623,516, which is a continuation of application No. 09/309,052, filed on May 10, 1999, now Pat. No. 6,440,158, which is a division of application No. 08/453,066, filed on May 26, 1995, now Pat. No. 5,902,268, which is a division of application No. 08/287,114, filed on Aug. 8, 1994, now Pat. No. 5,624,392, which is a continuation-in-part of application No. 07/929,305, filed on Aug. 13, 1992, now Pat. No. 5,342,301.

(51) Int. Cl.
*A61M 29/00* (2006.01)

(52) U.S. Cl. .................. 606/194; 604/96.01
(58) Field of Classification Search ............. 604/43–46, 604/96.01, 103.06–103.08, 104; 606/191, 606/192, 194
See application file for complete search history.

(56) References Cited

U.S. PATENT DOCUMENTS

| | | | |
|---|---|---|---|
| 4,299,226 A | | 11/1981 | Banka |
| 4,406,656 A | * | 9/1983 | Hattler et al. ............... 604/523 |
| 4,422,447 A | | 12/1983 | Schiff |
| 4,540,404 A | | 9/1985 | Wolvek |
| 4,681,092 A | | 7/1987 | Cho et al. |
| 4,820,349 A | * | 4/1989 | Saab ......................... 606/194 |
| RE32,983 E | | 7/1989 | Levy |
| 4,869,263 A | | 9/1989 | Segal et al. |
| 5,106,360 A | * | 4/1992 | Ishiwara et al. ................ 600/2 |
| 5,342,301 A | * | 8/1994 | Saab ..................... 604/103.13 |
| 5,569,195 A | * | 10/1996 | Saab ..................... 604/103.13 |
| 6,966,889 B2 | * | 11/2005 | Saab ....................... 604/96.01 |

FOREIGN PATENT DOCUMENTS

EP   0274411   11/1988

* cited by examiner

*Primary Examiner*—Nicholas D Lucchesi
*Assistant Examiner*—Theodore J Stigell
(74) *Attorney, Agent, or Firm*—David Silverstein Andover-IP-Law

(57) ABSTRACT

Multi-lumen balloons for use as or in conjunction with balloon dilation catheters, and methods for making such balloons, are disclosed.

31 Claims, 6 Drawing Sheets

MULTI-LUMEN CATHETERS AND METHODS FOR USING SAME

This application is a division of U.S. patent application Ser. No. 10/259,117, filed Sep. 27, 2002, now U.S. Pat. No. 6,966,889, issued Nov. 22, 2005, which was a continuation-in-part of U.S. patent application Ser. No. 10/011,137,filed Dec. 7, 2001, now U.S. Pat. No. 6,623,516, issued Sep. 23, 2003, which is a continuation of U.S. patent application Ser. No. 09/309,052, filed May 10,1999, now U.S. Pat. No. 6,440,158, issued Aug. 27, 2002, which is a division of U.S. patent application Ser. No. 08/453,066, filed May 26, 1995, now U.S. Pat. No. 5,902,268, issued May 11, 1999; which in turn was a division of U.S. patent application Ser. No. 08/287,114, filed Aug. 8, 1994, now U.S. Pat. No. 5,624,392, issued Apr. 29, 1997; which was in turn a continuation-in-part of U.S. patent application Ser. No. 07/929,305, filed Aug. 13, 1992, now U.S. Pat. No. 5,342,301, issued Aug. 30, 1994. The disclosures of each of the above-identified patents and patent applications are incorporated herein by reference.

The present invention relates generally to balloons and balloon catheters for internal body applications, and more particularly, to balloons having a plurality of lumens through which to access either the distal end of the catheter shaft or internal body-locations, and to methods of making such multi-lumen balloons.

BACKGROUND OF THE INVENTION

The use and construction of balloon catheters is well known in the medical art, as described for example in U.S. Pat. No. Re. 32,983 (Levy) and U.S. Pat. No. 4,820,349 (Saab). Balloon catheters are typically utilized as dilatation devices for dilating a blood vessel, e.g. a coronary artery, or other body cavity, although other uses have been developed, e.g., temporarily anchoring an instrument within a body lumen so that a surgical or therapeutic procedure can be performed. Other patents generally showing the application of various types of balloon catheters include U.S. Pat. No. 4,540,404 (Wolvek), U.S. Pat. No. 4,422,447 (Schiff), and U.S. Pat. No. 4,681,092 (Cho et al.).

It is also well known in the medical art to employ catheters having shafts formed with a plurality of lumens in instances where it is necessary or desirable to access the distal end of the catheter or a particular internal body location simultaneously through two or more physically separate passageways. For example, U.S. Pat. No. 4,576,772 (Carpenter) is directed to increasing the flexibility: or articulatability of a catheter having a shaft formed with a plurality of lumens that provide distinct conduits for articulating wires, glass fiber bundles, irrigation, and vacuum means.

It is also known, as shown in U.S. Pat. No. 4,299,226 (Banka) and U.S. Pat. No. 4,869,263 (Segal et al.), to employ multi-lumen catheters with a balloon. The Banka patent shows a double-lumen catheter shaft of coaxial construction wherein the outer lumen carries saline solution to inflate a balloon, and an inner lumen, located coaxially inside the outer lumen, is adapted to receive a stylet or guide wire. In the Banka patent, the double-lumen dilatation catheter is designed to be coaxially contained within the single lumen of a larger diameter guide catheter.

The Segal et al. patent shows a more complex dilatation catheter having five separate, non-coaxial lumens (FIGS. 1 and 2) extending through the catheter shaft, including a balloon inflation lumen 18, a distal lumen 17, a wire lumen 22, a pulmonary artery lumen 26, and a right ventricular lumen 28. Lumens 17 and 18 extend the entire length of the catheter shaft from the proximal extremity to the distal extremity. Lumen 17 exits through the distal extremity 14b of the catheter shaft. The distal extremity of lumen 18 is in communication with the interior of balloon 16 to permit inflation and deflation. Lumens 22, 26 and 28, on the other hand, only pass partly or completely through the larger diameter, proximal portion 14a of the catheter shaft. A transducer 21 mounted at the transition-between portions 14a and 14b is coupled to circuitry by wires 24 extending through wire lumen 22. Proximal portion 14a is stated to have a diameter of, for example, 0.098 inches whereas distal portion 14b has a diameter, for example, of 0.060 inches. The Segal et al. catheters are prepared by extrusion (col. 2, lines 53-54).

In the above-cited prior art, it should be appreciated that the term "multi-lumen" in the phrase "multi-lumen balloon catheters" means that the catheter shaft is multi-lumen (as opposed to the balloon secured to the shaft). In accordance with the present invention, it is the balloon itself that is multi-lumen. It is believed that there are many applications where an inflatable balloon having multiple, distinct channels or lumens that are formed as a part of the inflatable balloon would be very desirable. As used herein, the terms "balloon" and "balloon lumen" therefore mean a thermoplastic tubular segment having the properties of being very thin-walled (less than 0.0015 inches thick), high strength, flexible, readily inflatable under a predetermined range of fluid pressures, and readily collapsible under vacuum. It is also typical for such balloons to have at least one tapered end, although according to the present invention it is not necessary. For high strength, these balloons are normally expanded and oriented in at least one direction and preferably in two directions, i.e. biaxial orientation. Orientation occurs when a thermoplastic material is expanded or stretched under certain conditions with the result that the material has a much greater strength than before expansion. Such balloons, and methods of preparing them, are described in U.S. Pat. No. 4,820,349 (Saab), U.S. Pat. No. Re. 32,983 (Levy), and European Patent Specification No. 0274411 (Saab), which are incorporated herein by reference. For some applications, a balloon segment having the general properties described above can be affixed to an elongated, relatively thick-walled (0.002 inches or thicker) catheter shaft. For other applications, the elongated, thin, side walls of the balloon can serve as the catheter shaft when the balloon is inflated.

The multi-lumen balloons of the present invention are distinguished from the multi-lumen balloon catheters of the prior art, as discussed above, in that the walls defining the lumens are formed as an integral part of the balloon. As used herein, the terms "integral part" and "integrally formed" each mean that each lumen of the multi-lumen balloon shares a common wall portion with part of at least one balloon lumen. By contrast, the prior art shows lumens that are integrally formed as a part of a conventional catheter shaft and are defined by relatively thick walls of that shaft (e.g. Segal et al.), catheter lumens that communicate with or terminate in a balloon segment (e.g. Banka and Segal et al.), and lumens in a shaft that passes coaxially through a balloon segment (e.g. Banka). The relatively thick walls that define the lumens of conventional multi-lumen catheter shafts typically range from about 0.002-0.010 inches in wall thickness and, in any event, are not high tensile strength or readily inflatable under fluid pressure, nor are they readily collapsible under vacuum when operating at the pressures for which the device is designed. Most balloon catheter shafts are made by extrusion of a thermoplastic material. The resulting shafts are typically not substantially oriented, therefore not high tensile strength. Such balloon catheter shafts are not inflatable as balloons at pressures at which the balloons typically operate, for the obvious reason that the shafts are supposed to remain stiff, and not inflate or deflate. Thus, the multi-lumen catheters of the prior art cannot, by themselves, function as balloons. As a result the design of multi-lumen catheters which use balloons has been limited because these features provide design constraints.

For example, a perfusion-catheter utilizes a balloon to perform an angioplasty procedure to dilate coronary arteries which are partially closed due to arteriosclerosis. While this procedure is often effective in relieving the symptoms caused by the disease by dilating the blood vessels for a substantial length of time, it will be evident that the balloon itself will occlude the blood vessel while it is inflated within the vessel. Accordingly, perfusion catheters are equipped with at least one additional lumen extending through the catheter shaft. The shaft is provided with openings that communicate with this additional lumen on opposite sides of the balloon (the sides of the shaft both distal and proximate from the balloon) so that blood will flow though the lumen when the balloon is inflated reducing the risks to the patient. However, the shaft is typically of a small cross-sectional diameter, with the perfusion lumen being even smaller so that blood flow is still substantially reduced.

These and other limitations of the prior art catheters are overcome with the multi-lumen balloons of this invention.

OBJECTS OF THE INVENTION

Accordingly, it is a principal object of this invention to provide multi-lumen balloons for use as, or in conjunction with, balloon catheters.

It is also an object of this invention to provide a multi-lumen balloon wherein the walls of the lumens are integrally formed as a part of the balloon.

A further object of this invention is to provide multi-lumen balloons wherein the lumens may be open or closed ended, of varying sizes and geometries, and may begin and end at varying longitudinal positions along the axes of the balloons.

Another object of this invention is to provide multi-lumen balloons wherein the individual lumens may be utilized, among other things, for drainage; for circulating heat transfer fluids; for housing electrical or guide wires or laser fibers; for accessing internal body locations with fluids, medicine, drugs, or medical instruments; and for facilitating passage of fluids, such as blood, around an obstruction including the balloon itself.

Still another object of this invention is to provide multi-lumen balloons wherein the materials used to form the individual lumens may have different physical and/or chemical properties from each other.

Yet another object of this invention is to provide methods of preparing multi-lumen balloons in accordance with this invention.

And still another object of the present invention is to provide an improved balloon catheter provided with a multi-lumen balloon as described.

These and other objects and advantages of this invention will be better understood from the following description, which is to be read together with the accompanying drawings.

SUMMARY OF THE INVENTION

The balloon of the present invention comprises thin walled, inflatable, flexible, thermoplastic tubular material formed so as to define at least two separate channels or lumens integrally formed with one another. At least one of the lumens can be inflatable with a fluid. Such balloons can be prepared by a blow molding process utilizing multi-lumen tubing or preforms. Alternatively, an outer balloon segment can be formed by blow molding the segment from tubing or a preform in a mold. Forming wires or mandrels can then be positioned in contact with the inner surface of the outer balloon and a second tube or preform is blown into contact with the inner wires or mandrels and the inner surface of the outer balloon segment. The balloons also can be fabricated by heat shrinking a heat-shrinkable thermoplastic film or tubing over one or more forming wires or mandrels positioned along an outer wall of an inner balloon preform, or by heating and expanding thermoplastic tubing along an inner wall of a balloon. Additionally, the blow molding and heat shrinking processes can be combined. Depending on the fabrication process selected, the lumens can be located inside or outside the balloon and made open or closed ended, of varying sizes and geometries, positioned at different locations along the balloon, and having different physical and/or chemical properties.

DETAILED DESCRIPTION OF THE INVENTION

In all of the drawings, as described below, it should be understood that the wall thicknesses have been greatly exaggerated relative to other elements and dimensions for purposes of illustration.

Figure 1A:
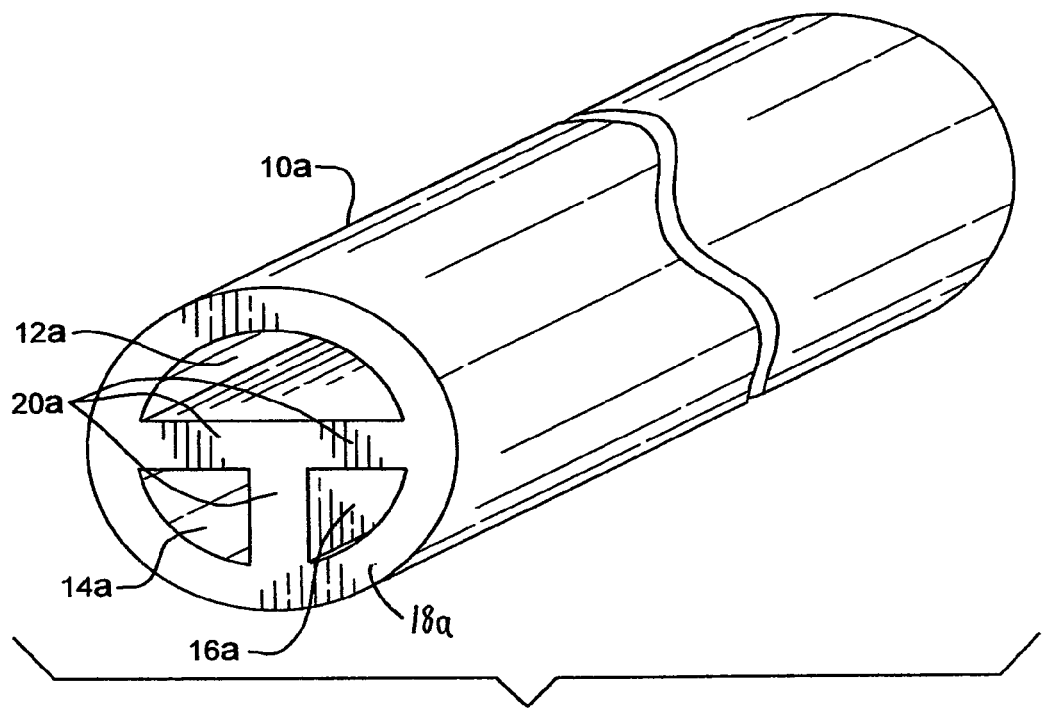
FIG. 1A is a partial isometric view of a three-lumen tube or preform according to one embodiment of the invention.
Figure 2A:
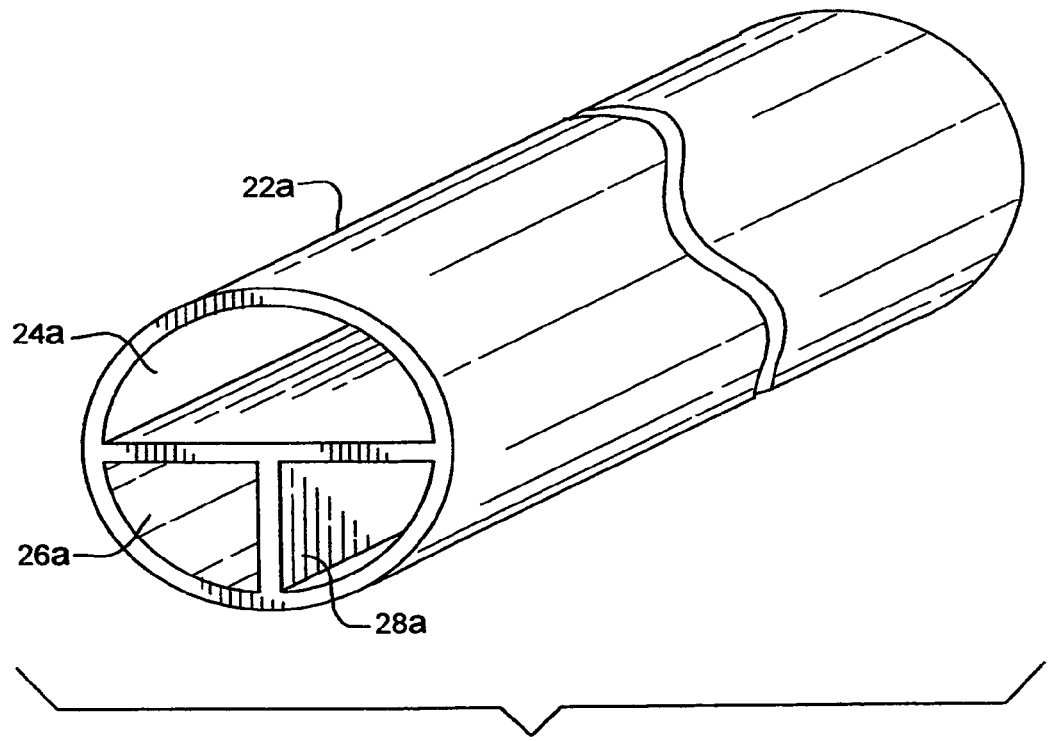
FIG. 2A is a partial isometric view of a three-lumen balloon prepared by blow molding the preform of FIG. 1A.
Figure 1B:
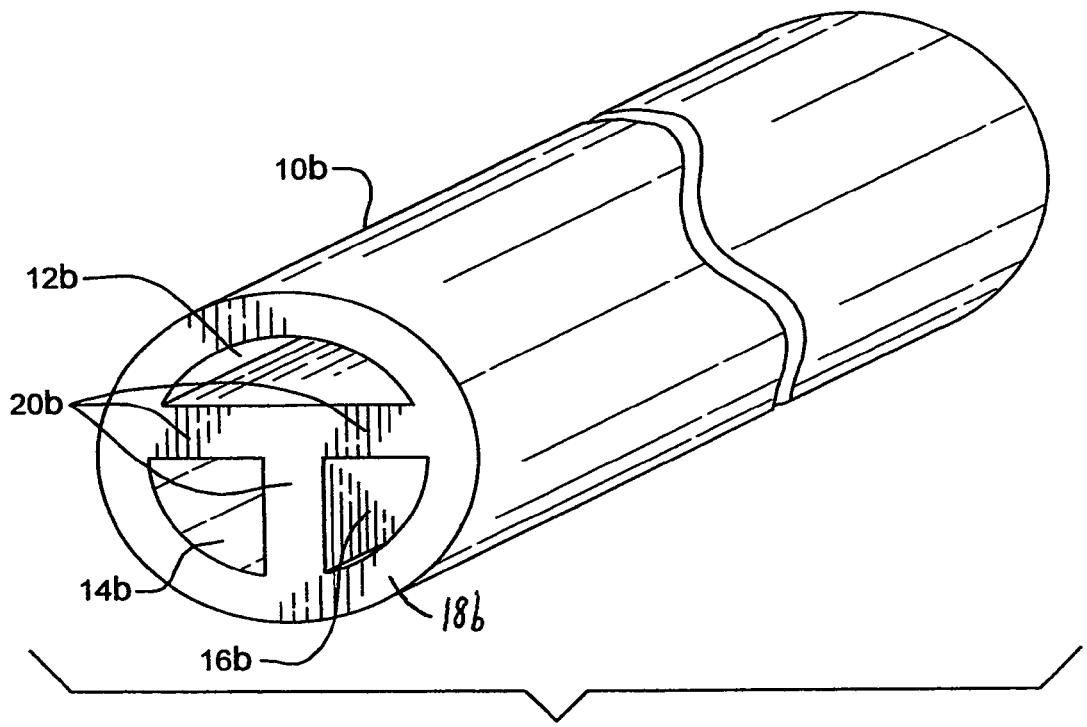
FIG. 1B is a partial isometric view of a three-lumen tube or preform according to another embodiment of the invention.
Figure 2B:
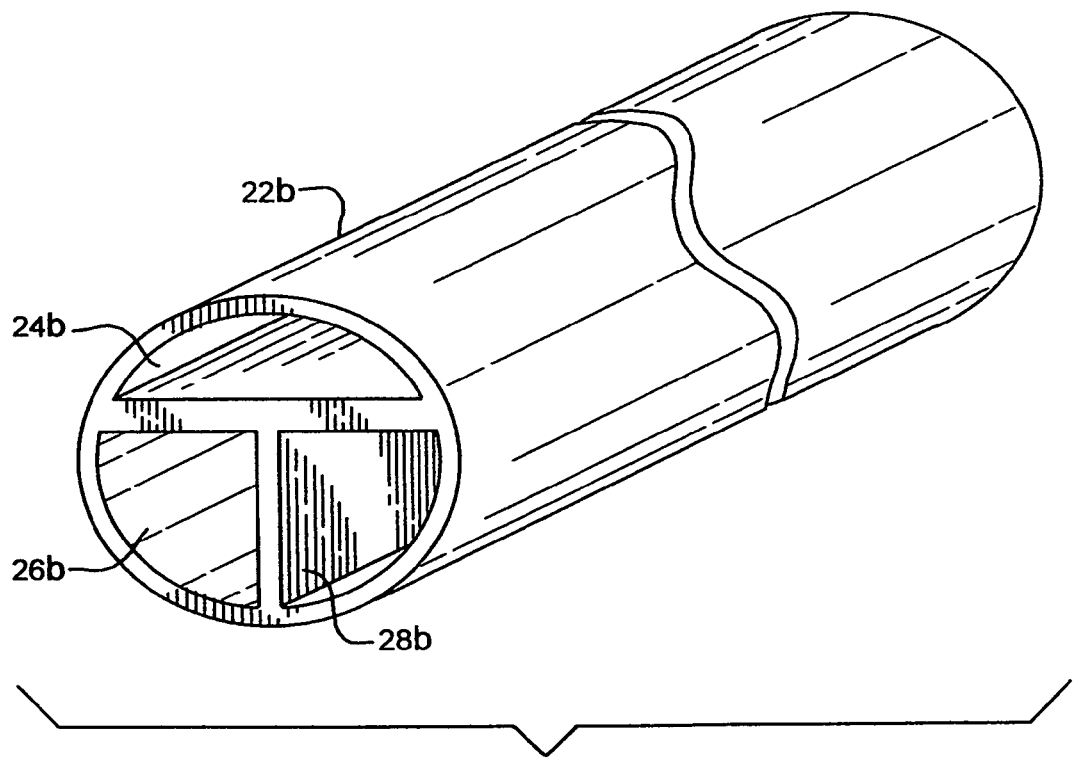
FIG. 2B is a partial isometric view of a three-lumen balloon prepared by blow molding the preform of FIG. 1B.
Figure 1C:
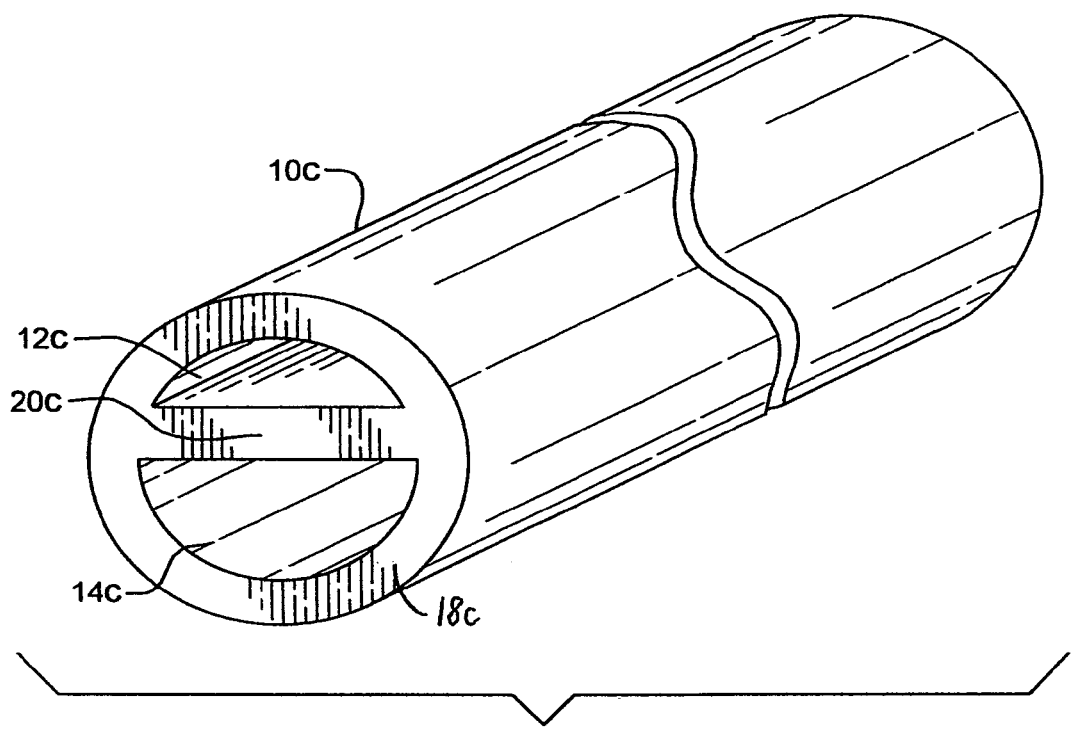
FIG. 1C is a partial isometric view of a two-lumen tube or preform according to another embodiment of the invention.
Figure 2C:
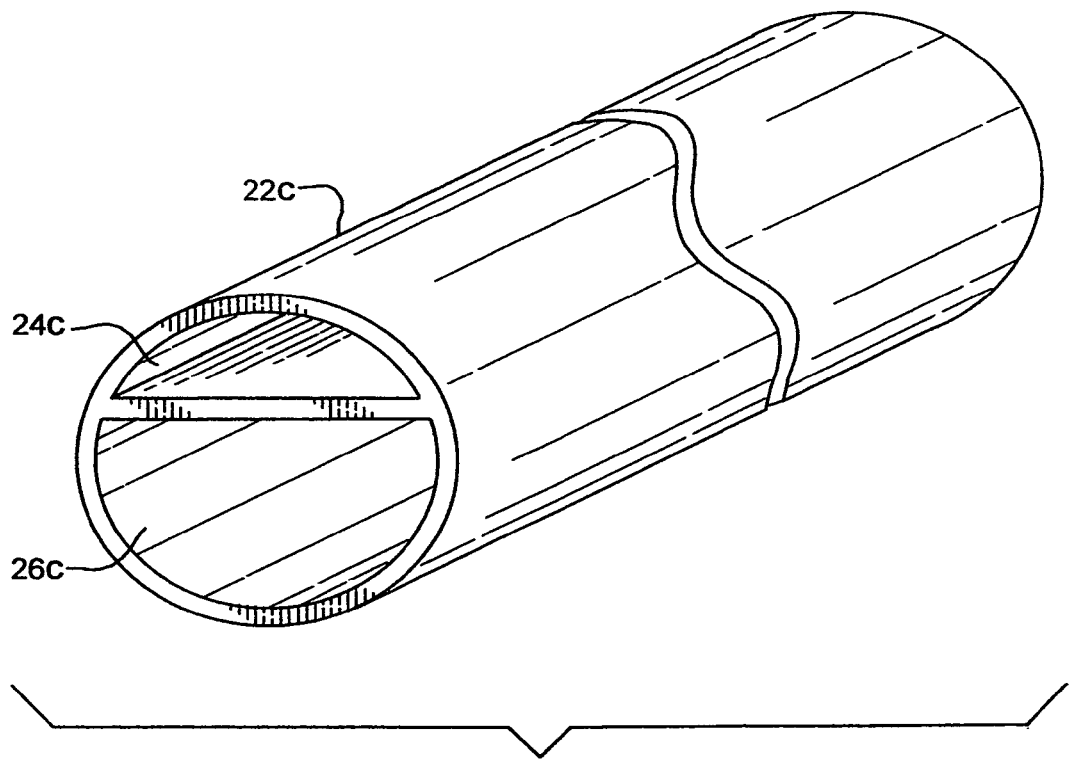
FIG. 2C is a partial isometric view of a two-lumen balloon prepared by blow molding the preform of FIG. 1C.

FIG. 1A shows a partial isometric view of a thermoplastic tube or preform 10a according to one embodiment of the invention comprising three independent preform channels or lumens 12a, 14a and 16a. FIG. 1B shows a partial isometric view of a thermoplastic tube or preform 10b according to another embodiment of the invention comprising three independent preform channels or lumens 12b, 14b and 16b. FIG. 1C shows a partial isometric view of a thermoplastic tube or preform 10c according to another embodiment of the invention comprising two independent preform channels or lumens 12c and 14c. Thermoplastic preforms such as that illustrated in the invention embodiments of FIGS. 1A, 1B and 1C are the starting point for one method of preparing multi-lumen balloons in accordance with this invention. Such multi-lumen preforms can be prepared using conventional technologies such as extrusion. The extrusion method can be used to produce tapered lumen sections. Co-extrusion of various materials is also well known in the art and can be used to produce preforms suitable for this invention. Additionally, extrusion techniques that allow one to open and seal off a lumen so that the lumen can start and stop at any selected axial location can be used to produce suitable preforms. As shown in FIG. 1A for illustrative purposes, the three preform lumens 12a 14a and 16a are shaped so that each of the walls are of a thickness substantially in proportion to the final thickness of the walls of the formed lumens after the balloon is formed. The thickness of the walls of the tubular material of the preform can be the same as that typically employed for catheter shafts, between about 0.002 and 0.010 inches, although this can vary. These walls include the cylindrical wall 18a, as well as the interior walls 20a, which may or may not be radially directed. In this example, the three interior walls 20a are each radially directed, and two of those interior walls 20a are aligned to form a diametric wall or chord that bisects the interior of the cylinder. Also, the cylindrical wall 18a may be thicker than the interior walls 20a when it is desired that the final wall thickness of the cylindrical wall of the balloon is to be thicker. As shown in FIG. 1B for illustrative purposes, the three preform lumens 12b, 14b and 16b are substantially similar to preform lumens 12a, 14a and 16a respectively in FIG. 1A. except that the two aligned interior walls 20b are not radially directed as in FIG. IA and, instead, form a chord wall that does not bisect the interior of the cylinder. As shown in FIG. 1C for illustrative purposes. preform lumen 12c is substantially similar to preform lumen 12b in FIG. 1B, but, by omitting the third interior wall 20b in FIG. 1B, lumens 14b and 16b of FIG. 1B become a large single lumen 14c in FIG. 1C. The geometry of the preform and the preform lumens determines, at least in part, the geometry of the resulting multi-lumen balloons. It will be understood that, depending on the type of multi-lumen balloon desired, the starting preform can be selected to have more or less than three preform lumens (with a minimum of two lumens as shown in Fig. 1C for example), lumens of varying dimensions, and lumens with tapered sidewalls. Such different preforms can be prepared with well known technologies. Blow molding a portion of the preform 10a of FIG. 1A, 10b of FIG. 1B, or 10c of FIG. 1C, in accordance with conventional balloon fabrication techniques, for example as described in U.S. Pat. No. 4,820,349 (Saab),U.S. Pat. No. Re. 32,983 (Levy), and European Patent Specification No. 0274411 (Saab), results in a very thin-walled, flexible, high strength balloon lumens that comprise balloon elements 22a, 22b or 22c as shown respectively in FIGS. 2A, 2B or 2C. In the course of the blow molding operation preform lumens 12a, 14a and 16a of FIG. 1A (or 12b, 14band 16b of FIG. 1B; or 12c and 14c of FIG. 1C) are oriented into three very thin-walled, flexible, high strength balloon lumens 24a, 26a and 28a respectively in FIG. 2A (or 24b, 26b and 28b in FIG. 2B; or 24c and 26c in FIG. 2C), each integrally formed with at least a portion of one wall of another balloon lumen and preferably, although not necessarily, running the length of the balloon (including its tapered end or ends if the balloon is provided with one, similar to that shown in FIG. 3). In the embodiment shown, all of the walls are sufficiently thin, i.e., 0.00 15 inches or less so that the lumens are each selectively inflatable, although as stated above it is possible that, for some annlications. one or more of the walls is of a thickness greater than 0.002 inches so that fewer than all of the lumens are inflatable. It will be understood that the diameter of balloon elements 22a, 22b or 22c, when fully expanded, will be substantially greater than the starting diameter of preform 10a, 10b or 10c, respectively (typically 2-6 times greater).

The foregoing method for preparing multi-lumen balloons in accordance with this invention is especially well suited to producing lumens that run along the entire axial length of the balloon and in situations where precise lumen geometry is not critical. In addition, this process can produce the thinnest and most flexible multi-lumen balloons because the walls are each of a single wall thickness, rather than portions of the walls having the thickness of a double wall as results from the alternative embodiment described below.

Figure 3:
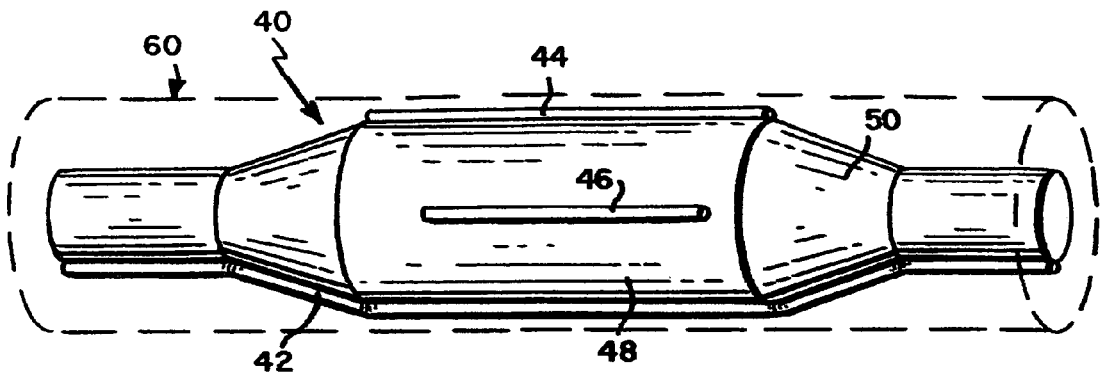
FIG. 3 is an isometric view of a balloon with three forming wires of varying lengths positioned longitudinally along the exterior of the balloon wall and with a surrounding heat-shrinkable tube shown in dotted outline.
Figure 4:
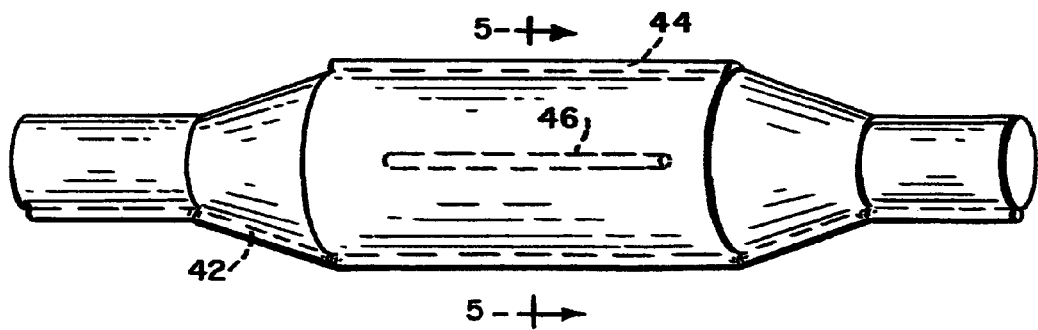
FIG. 4 is an isometric view of the balloon of FIG. 3 following the heat shrinking process to create three perimetrical lumens following the removal of the forming wires and forming ribbed protrusions from the exterior wall of the balloon.
Figure 5:
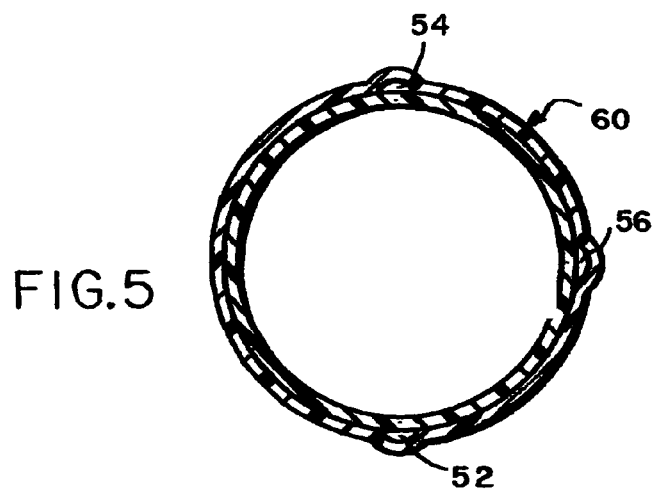
FIG. 5 is a cross-sectional view of the three-lumen balloon of FIG. 4 along the line 5-5.

FIGS. 3-5 illustrate an alternative embodiment of this invention wherein multi-lumen balloons are prepared by heat-shrinking a thermoplastic film or thin-walled tubing over one or more forming wires or forming mandrels positioned along an outer wall of a previously-formed balloon 40. The previously formed balloon can be formed in a mold so as to form the continuous structure shown and described below in connection with FIG. 3. However, the starting balloons for this embodiment of the invention can be prepared by any conventional technique, such as that described in U.S. Pat. No. 4,820,349 (Saab), U.S. Pat. No. Re. 32,983 (Levy), and European Patent Specification No. 0274411 (Saab). A mandrel (not shown) may be positioned inside the balloon for support. Alternatively the balloon may be filled with a pressurized fluid for support.

Thus, forming wires or mandrels 42, 44 and 46 in FIG. 3, are positioned in a longitudinal direction along the outer wall of balloon 40. As seen in FIG. 3, the wires may be of varying lengths and may start and end at different longitudinal locations along the axis of the balloon. For example, in FIG. 3, forming wire 42 runs the entire length of the balloon 40 including the working section 48 and the tapered ends or transition cones 50, and will create a lumen 52, as best seen in FIG. 5, that also runs the length of the balloon including the conical or tapered ends 50. Forming wire 44, on the other hand, runs from one end of the balloon across working section 48 and will create a corresponding lumen 54 as seen in FIG.

5. Finally, forming wire 46 begins and ends along the outer wall of the balloon within working section 48 without either end of wire 46 extending to an end of the balloon, thereby creating a corresponding lumen 56 as seen in FIG. 5. The forming wires may be of the same or different diameters, and may be of a uniformed cross-section or a non-uniformed cross-section such as a taper, and may be of circular or other cross-sectional shape, depending on the desired lumen geometry. Thus, for example, this method permits the manufacture of balloons with lumens of generally circular, ovular, triangular or rectangular cross-sections to accommodate different needs. The geometric cross-section of each wire can also change in cross-sectional size or shape along its length as may be required for a particular application.

When the forming wires have been properly positioned along the outer wall of balloon 40, suitably held in place for example by proper placement within a fixture, a tube 60 of a heat-shrinkable thermoplastic, such as a biaxially-oriented polyethylene terephthalate, having a diameter somewhat greater than that of balloon 40 is slipped over the balloon and the forming wires. The actual diameter of the tube 60 should be as close as possible to the final dimension to maintain the strength. A suitable tool, such as a mandrel can be secured within the inner balloon 40 so that the latter maintains its shape. Alternatively, the balloon may be filled with a pressurized fluid for support. When tube 60 is subjected to heat treatment, the tube shrinks to come into intimate contact with and conform to outer wall 48 of balloon 40, except where forming wires 42, 44 and 46 cause tube 60 to conform outwardly from the outer wall of the balloon as it forms around the wires thereby creating lumens 52, 54 and 56 respectively, each integrally formed with the wall 48 of the balloon 40. The balloon and tube can but need not be bonded together using a suitable adhesive, such as a solvent-based flexible polyester hot melt adhesive. Removal of wire 42 leaves a lumen 52 open at both ends. Removal of wire 44 can leave a lumen 54 open at one end and closed at the other. Removal of wire 46 requires cutting open at least one closed end of lumen 56.

The foregoing method of preparing multi-lumen balloons in accordance with this invention is the preferred embodiment in most cases for producing perimetrical lumens forming ribbed protrusions from the exterior wall of the multi-lumen balloon. Such a design is useful where the multi-lumen balloon is to be inserted in a body lumen, and the main lumen formed by the inner balloon 40 is inflated such that inflation of the balloon 40 will have little or no effect on the pressure within the perimetric lumens 52, 54 and 56 protruding from the outer surface of the final multi-lumen balloon design because balloon 40 is substantially inelastic. This embodiment also illustrates that at least some of the lumens do not need to run the entire length of the balloon. This is also the preferred embodiment where relatively precise lumen geometry and dimensions are important. Selection of the mandrels or forming wires in this embodiment permits relatively precise control over the size, shape and location of the lumens and makes the results highly reproducible. This embodiment also facilitates producing lumens with somewhat different properties than the balloon. For example, for many applications it may be desirable to use a balloon 40 of high strength PET, but to choose a tube 60 made of thin-walled, heat-shrinkable polyethylene which would create polyethylene lumens and a very low friction outer shell for the multi-lumen balloon. The tubing 60 on the other hand can be made of biaxially oriented polyethylene terephthalate.

Figure 6:
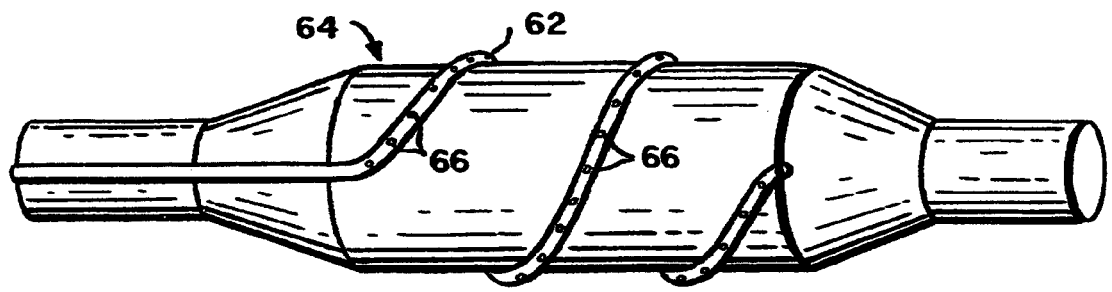
FIG. 6 is an isometric, view of a multi-lumen balloon formed with a helical perimetric lumen having pin holes for delivering fluid to a body cavity.

This embodiment of the invention also makes it possible to easily form a balloon having a perimetrical lumen 62 running, for example, in a helical pattern around the cylindrical wall of the balloon 64, as best shown in FIG. 6. Such a spiral perimetrical lumen can contain pinholes 66 along its length and can be used to precisely deliver medications or other fluids to select locations within the body cavity within which the balloon is placed, while at the same time independently providing balloon dilatation obviously, the geometric shape of such a lumen need not necessarily be helical, but can assume any conceivable shape for the particular application for which it is to be used.

Figure 7:
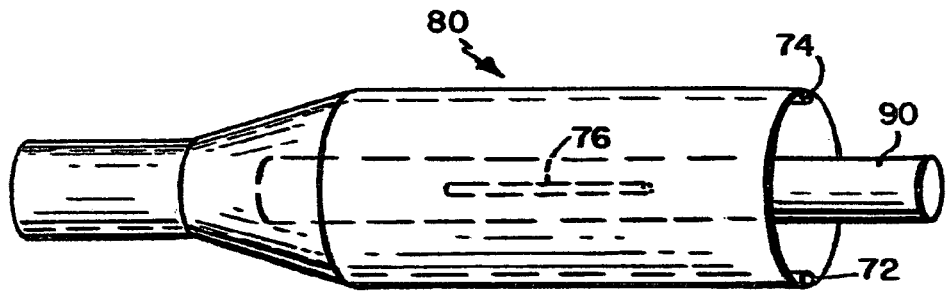
FIG. 7 is an isometric view of an outer balloon with three forming wires of varying lengths positioned longitudinally along the interior of the balloon wall and with a preform tube shown within the outer balloon in dotted outline.
Figure 8:
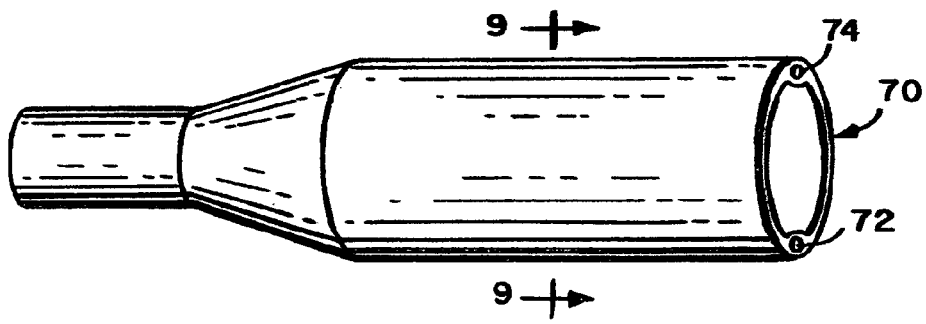
FIG. 8 is an isometric-view of the balloon of FIG. 6 following the heat expansion of the inner preform to create three interior, perimetrical lumens following the removal of the forming wires.
Figure 9:
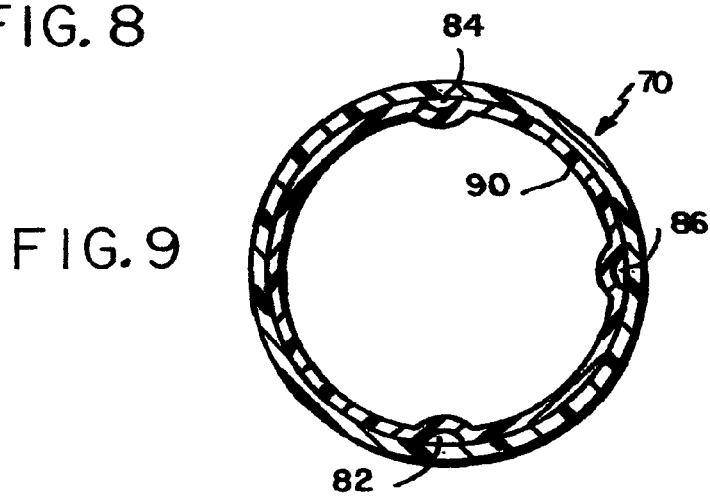
FIG. 9 is a cross-sectional view of the three-lumen balloon of FIG. 8 along the line 9-9.

FIGS. 7-9 show a method of making a multi-lumen balloon 70 having three perimetrical lumens which protrude inwardly into the larger lumen. Forming wires of varying lengths may be positioned longitudinally along the interior of the balloon wall and with a preform tube 90 shown within the outer balloon 80 in dotted outline. In this embodiment the outer balloon 80 is preformed in the same manner as was inner balloon 40 shown in FIGS. 3-5. The balloon can be blown in a mold where it is ready to receive the wires 72, 74 and 76 (which are comparable to wires 42, 44 and 46, respectively) and the inner preform tube 90. In this instance the inner tube 90 is blown so that it comes into contact with the wires and the inner surface of the balloon 80. The two pieces can but need not be secured together and the wires 72, 74, 76 removed in the same manner as described in connection with FIGS. 3-5 so as to form three perimetrical lumens 82, 84 and 86, all protruding inwardly. In this embodiment, inflation of the expanded inner tube 90 of the resulting multi-lumen balloon will tend to collapse and squeeze the smaller lumens 82, 84 and 86. This embodiment can be used, for example, to "clamp" down on an object, such as a guide wire or fiber optic, during inflation of the balloon.

Figure 10:
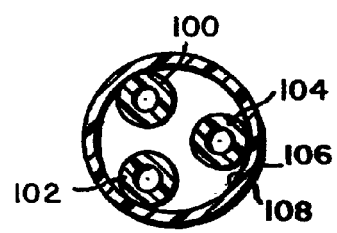
FIG. 10 is a cross-sectional view of a balloon enclosing three sections of expandable tubing.
Figure 11:
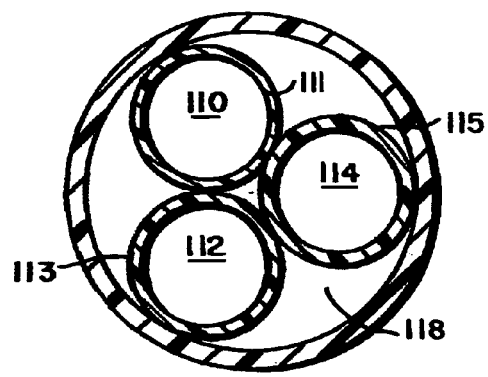
FIG. 11 is a cross-sectional view similar to FIG. 10, but showing the balloon following expansion of the tubing to form three substantially circular interior lumens and one irregularly-shaped interior lumen.

Still another embodiment of this invention is illustrated in FIGS. 10 and 11 wherein multi-lumen balloons are prepared by heating and expanding one or more sections of thermoplastic tubing within the inner wall of a preformed balloon. The starting balloons for this embodiment of the invention can be prepared by any conventional technique, such as that described in U.S. Pat. No. 4,820,349 (Saab), U.S. Pat. No. Re. 32,983 (Levy), and European Patent Specification No. 0274411 (Saab). Thus, in FIG. 10, tubing sections 100, 102 and 104 are positioned inside balloon 106 defined by inner wall 108. Upon expansion of tubing sections 100, 102 and 104, as seen in FIG. 11, they create respectively generally circular lumens 110, 112 and 114, defined respectively by walls 111, 113 and 115. Walls 111, 113 and 115, together with inner wall 108, define an irregularly-shaped balloon lumen 118. This method for preparing multi-lumen balloons is useful for producing interior lumens and wherein it is desired to have lumens with different physical and/or chemical properties from the balloon or from each other or both.

EXAMPLE

A 4 mm balloon with only one tapered end was fabricated from PET using conventional techniques. The balloon was placed over a mandrel for support and a wire rod (0.028" diameter) was laid up against the outside of the balloon. A piece of biaxially-oriented, thin walled, high strength polyester shrink tube was placed over the entire assembly and shrunk over the balloon and wire. The assembly was cooled and the wire and support mandrel removed resulting in a 4 mm balloon with an 0.028" "side lumen" on the outside of the balloon. In this case the placement of the wire end determined where the lumen ended along the balloon.

The multi-lumen balloon/catheter constructions of this invention can be used with virtually any catheter or balloon/catheter design including over the wire, fixed wire, rapid exchange, and other conventional as well as non-traditional catheter designs. In addition, the multi-lumen balloons of this invention facilitate the production of an entirely new and distinctive generation of catheter designs.

One example of the many benefits of this invention is in balloon angioplasty, which involves inserting a balloon dilatation catheter into a coronary artery that contains an occluded section and inflating the balloon segment at the occlusion site to open a larger arterial passageway. During the inflation procedure, blood flow in the damaged artery is temporarily blocked by the inflated balloon, which can be hazardous or fatal and therefore limits the dilatation time. To alleviate this problem and extend dilatation time to improve effectiveness, so-called perfusion catheters have been developed wherein holes in the catheter shaft on either side of the balloon permit a small volume of blood to enter the interior of the catheter shaft, by-pass the balloon, and exit the catheter shaft on the other side.

Because of the relatively small diameter of the catheter shaft, however, the volume of blood that can by-pass the balloon in this fashion is minimal unless the shaft is very large. However, such larger diameter shafts have increased profiles and stiffness; and, as a result, the existing perfusion catheters are of limited utility. By contrast, with the multi-lumen balloons of this invention, one or more interior balloon lumens can be utilized to open a by-pass almost as large as the blocked artery itself, thereby greatly increasing blood flow and extending dilatation time. Indeed, once in place, a multi-lumen balloon used in this manner could be kept inflated for days and act as a temporary stent.

Figure 12:
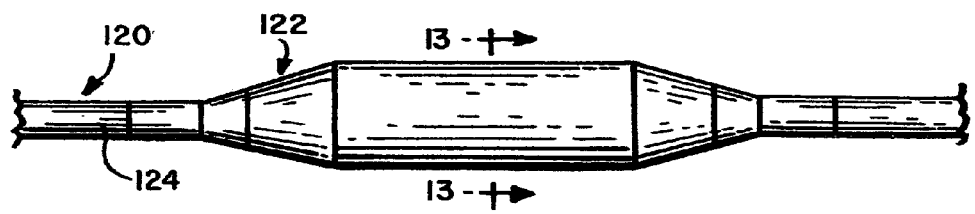
FIG. 12 is an isometric view of one embodiment of a perfusion catheter including a multi-lumen balloon made in accordance with the present invention.
Figure 13:
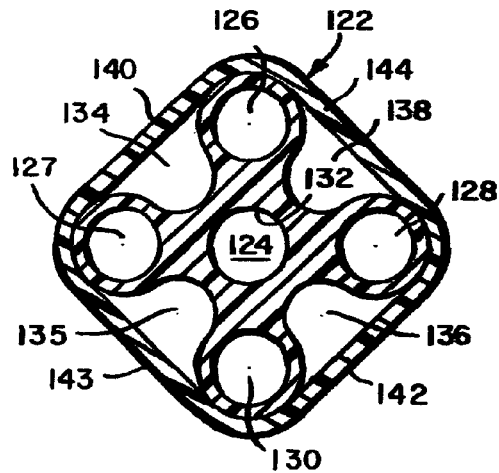
FIG. 13 is a cross-sectional view taken along section line 13-13 of the multi-lumen balloon shown in FIG. 12, wherein the balloon is made according to one method of the present invention.
Figure 14:
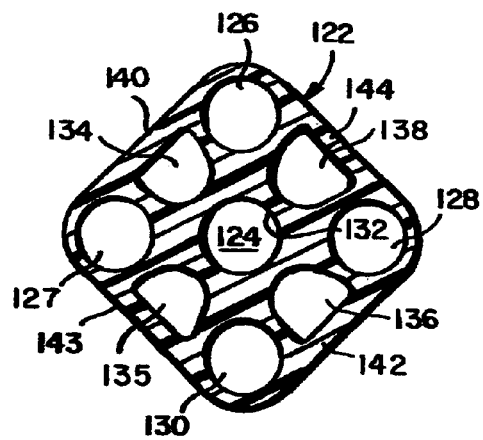
FIG. 14 is a cross-sectional view taken through a section line similar to section line 13-13 of the multi-lumen balloon shown in FIG. 12, wherein the balloon is made according to another method of the present invention.

For example, in FIGS. 12-14, a perfusion catheter 120 is designed with a multi-lumen balloon 122 in accordance with the principles of the present invention. In this design, the catheter shaft 124 is of a conventional design, except that it does not have to be provided with lumens for allowing for blood flow when the balloon is inflated. Instead the balloon is formed as a multi-lumen balloon in accordance with the present invention for providing the necessary blood flow, and for providing the necessary inflation so as to achieve dilatation of the blood vessel. As seen in FIG. 13, center lumen 132 receives the catheter shaft 124 so that the balloon can be secured in place with a suitable adhesive to the shaft. At least four lumens 126, 127, 128 and 130 are radially spaced about center lumen 132 for receiving the pressurized fluid for inflating each of these lumens so as to achieve dilatation of a blood vessel. The lumens 126, 127, 128 and 130, must be closed or connected and be adapted to be in fluid communication with a source of pressurized fluid. Lumens 134, 135, 136 and 138, are-formed within the spaces between lumens 126, 127, 128 and 130, and the corresponding wall sections 140, 143, 142 and 144, when lumens 126, 127, 128 and 130 are inflated. Lumens 134, 135, 136 and 138 are open at both the proximal and distal ends so that when lumens 126, 127, 128 and 130 are inflated with pressurized fluid, the wall sections 140, 143, 142 and 144 will become sufficiently taut so as to open lumens 134, 135, 136 and 138 and so as to allow blood to flow through these lumens. It should be appreciated that this catheter design can be used for other applications, for example where it is desirable to flush an area of the body cavity distal with respect to the balloon. In this case one of the lumens 134, 135, 136 or 138 can be used, or an additional lumen can be formed, so as to deliver the flushing fluid to the particular location of the body cavity, while the opened lumens allow for the flushing fluids to be easily removed.

The multi-lumen balloon for this embodiment can be made from two pieces, as shown in FIG. 13, or from a single integral piece, as illustrated in FIG. 14. The structure as shown in FIG. 13 can be prepared either by heat-shrinking a thermoplastic sleeve over the three-lobe interior structure (made by blow molding a five-lumen extruded preform of appropriate starting geometry in accordance with this invention) or by blow molding an extruded preform inside the thermoplastic sleeve. The structure as shown in FIG. 14 can be prepared by blow molding a nine-lumen extruded preform of appropriate starting geometry in accordance with this invention.

The multi-lumen balloons of this invention are also useful, for example, for producing guide wire lumens such that the guide wire need not pass through the catheter shaft and extend through the balloon interior, as is the case with typical prior art structures. Instead, with the multi-lumen balloons of this invention, the guide wire can be run, for example, in a secondary side lumen formed along the wall of the balloon and extending to a location distal with respect to the balloon.

One or more of any balloon materials can be used for the multi-lumen balloons of this invention including PET or other polyesters, nylon, PVC, polyethylene, etc. Thin-walled, high strength balloons such as PET, are preferred in most applications in order to minimize the overall profile (build up of wall thicknesses) of the final catheter devices.

The multi-lumen balloons of this invention can be used either by themselves as balloon dilatation catheters or as the balloon segment of a conventional balloon catheter. For example, one end of a balloon having two secondary lumens in accordance with this invention can be bonded to the distal end of a three lumen catheter such that each catheter lumen is in communication with the balloon or one of the secondary lumens respectively. The catheter lumen in communication with the balloon is used to inflate or deflate the balloon. A catheter lumen in communication with one of the secondary lumens can provide the access for fluids, drugs, a guide wire, laser or optical fibers, sensors, etc. For some applications, it may be desirable to bond both ends of the multi-lumen balloon to catheter segments having catheter lumens, for example for delivering medication, blood or other fluids to a point beyond an obstruction. In this case, a balloon having a secondary lumen that runs the length of the balloon and has two open ends can be connected to two catheter segments such that the proximal end of the secondary lumen communicates with a first catheter lumen and the distal end of the secondary lumen communicates with a second catheter lumen.

Other beneficial applications for the lumens of the multi-lumen balloons of this invention-include: means for additional dilatation of a body cavity by inflating and deflating secondary, tertiary or other balloon lumens; providing working channels to contain sensors, such as thermocouple or fiber optics, or to house guide wires; channels for the delivery of fluids, medicine or drugs to the area under the balloon or to regions beyond the balloon; working channels to house laser or optical fibers or a heating wire used to cauterize tissue; channels used for biopsy or other sampling procedures; channels used for drainage, for example as a urology drain; and channels used to circulate heat transfer fluids for cooling or heating purposes, such as freezing of select areas with liquid nitrogen or heating select areas with-heated fluid such as water or saline.

For example, with the multi-lumen balloons of this invention, a primary balloon lumen can be used for inflation while smaller, secondary lumens can contain a guide wire, thermocouple, laser fiber or optical fiber. In another example, a primary balloon lumen can be used to dilate a body cavity to a first size and shape; then, by dilating a secondary balloon lumen, the body cavity can be dilated to a second size or shape. For the latter embodiment, the secondary lumen must also have the general properties of a balloon, i.e., very thin-walled, flexible, high strength, readily inflatable under fluid pressure, and readily collapsible under vacuum.

As described above, depending on the method of fabrication, the lumens can be virtually any length, traveling from one end of the balloon to the other, or starting anywhere along the length of the balloon and ending anywhere. The lumens can be open or closed ended. The lumens can be made in a variety of shapes or cross-sections to accommodate different needs.

Since certain changes may be made in the above-described apparatuses and processes without departing from the scope of the invention herein involved, it is intended that all matter contained in the above description shall be interpreted in an illustrative and not in a limiting sense.

Having described the invention, what I claim is:

1. Multi-lumen medical balloon structure comprising a cylindrical region, defined by a cylindrical wall portion, divided into balloon lumens by planar wall portions, said wall portions each consisting essentially of an orientable thermoplastic polymer, at least a portion of which has been at least partially oriented by blow molding to form very thin-walled, flexible, high strength balloon lumens, said balloon structure comprising three or more such balloon lumens with substantially parallel longitudinal axes wherein each of said balloon lumens shares a common, integrally-formed at least partially oriented wall portion with at least one adjacent balloon lumen along at least a section of their respective axial lengths and further wherein at least one of said planar wall portions defines a chord across a cross section of the cylindrical region.

2. Multi-lumen medical balloon structure according to claim 1 wherein at least one of the lumens can be inflated with a fluid.

3. Multi-lumen medical balloon structure according to claim 1 wherein more than one of the lumens can be inflated with a fluid.

4. Multi-lumen medical balloon structure according to claim 1 wherein among said wall portions there is a thicker wall portion and other wall portions such that said thicker wall portion is thicker than the other wall portions.

5. Multi-lumen medical balloon structure according to claim 1 formed by blow molding at least a portion of a preform having at least three independent preform lumens.

6. Multi-lumen medical balloon structure according to claim 5 wherein among said wall portions there is a thicker wall portion of the preform and other wall portions such that said thicker wall portion is thicker than the other wall portions.

7. Multi-lumen medical balloon structure according to claim 1 wherein the lumens are selectively inflatable.

8. Multi-lumen medical balloon structure according to claim 1 wherein one or more of the wall portions is of a thickness such that fewer than all of the lumens are inflatable.

9. Multi-lumen medical balloon structure according to claim 1 wherein said wall portions include inner wall portions.

10. Multi-lumen medical balloon structure according to claim 9 wherein at least some of said inner wall portions are radially directed.

11. Multi-lumen medical balloon structure according to claim 9 wherein said inner wall portions are not radially directed.

12. A medical device for inflating an internal body region by providing multiple, inflatable lumens along all or at least a multi-lumen portion of said device, said device comprising a cylindrical region, defined by a cylindrical wall portion, divided into balloon lumens by planar wall portions, said wall portions each consisting essentially of an orientable thermoplastic polymer, at least a portion of which has been at least partially oriented by blow molding to form very thin-walled, flexible, high strength balloon lumens, said device comprising three or more such balloon lumens with substantially parallel longitudinal axes along at least said multi-lumen portion of said device wherein each of said balloon lumens shares a common, integrally-formed at least partially oriented wall portion with at least one adjacent balloon lumen along at least a section of their respective axial lengths and further wherein at least one of said planar wall portions defines a chord across a cross section of the cylindrical region.

13. A medical device according to claim 12 wherein at least one of the lumens can be inflated with a fluid.

14. A medical device according to claim 12 wherein more than one of the lumens can be inflated with a fluid.

15. A medical device according to claim 12 wherein among said wall portions there is a thicker wall portion and other wall portions such that said thicker wall portion is thicker than the other wall portions.

16. A medical device according to claim 12 formed by blow molding at least a portion of a preform having at least three independent preform lumens.

17. A medical device according to claim 12 wherein among said wall portions there is a thicker wall portion of the preform and other wall portions such that said thicker wall portion is thicker than the other wall portions.

18. A medical device according to claim 12 wherein the lumens are selectively inflatable.

19. A medical device according to claim 12 wherein one or more of the wall portions is of a thickness such that fewer than all of the lumens are inflatable.

20. A medical device according to claim 12 wherein said wall portions include inner wall portions.

21. A medical device according to claim 20 wherein at least some of said inner wall portions are radially directed.

22. A medical device according to claim 20 wherein said inner wall portions are not radially directed.

23. Medical apparatus for use as or in combination with a balloon dilatation catheter made by the method of blow molding at least a portion of a multi-lumen, tubular element with a cylindrical interior, defined by a cylindrical wall portion, which is divided into three or more preform lumens by planar wall portions, said tubular element comprising orientable polymer, so as to expand said preform lumens and to thereby orient the polymer in at least one direction thereby forming a tubular segment comprising multiple expanded lumens of at least partially oriented polymer wherein said expanded lumens have the properties of being flexible and sufficiently thin-walled that they are readily inflatable under fluid pressure and readily collapsible under vacuum, said expanded lumens having integrally formed wall portions that are integral with another lumen and further wherein at least one of said planar wall portions defines a chord across a cross section of the cylindrical interior.

24. Medical apparatus according to claim 23 wherein among said wall portions there is a thicker wall portion and other wall portions such that at least one of said lumens has the thicker wall portion characterized in that it is thicker than the other wall portions.

25. Medical apparatus according to claim 24 wherein the lumens are selectively inflatable.

26. Medical apparatus according to claim 23 wherein at least some of the lumens are defined at least in part by radially directed interior wall portions.

27. Medical apparatus according to claim 23 wherein the lumens are not defined by radially directed interior wall portions.

28. Medical apparatus according to claim 23 wherein one or more of the wall portions is of a thickness such that fewer than all of the lumens are inflatable.

29. Multi-lumen medical balloon structure comprising a cylindrical region, defined by a cylindrical wall portion, divided into balloon lumens by planar wall portions, said wall portions each consisting essentially of an orientable thermoplastic polymer, at least a portion of which has been at least partially oriented by blow molding to form very thin-walled, flexible, high strength balloon lumens, said balloon structure comprising two or more such balloon lumens with substantially parallel longitudinal axes wherein each of said balloon lumens shares a common, integrally-formed at least partially oriented wall portion with at least one adjacent balloon lumen along at least a section of their respective axial lengths and further wherein at least one of said planar wall portions defines a chord across a cross section of the cylindrical region.

30. A medical device for inflating an internal body region by providing multiple, inflatable lumens along all or at least a multi-lumen portion of said device, said device comprising a cylindrical region, defined by a cylindrical wall portion, divided into balloon lumens by planar wall portions, said wall portions each consisting essentially of an orientable thermoplastic polymer, at least a portion of which has been at least partially oriented by blow molding to form very thin-walled, flexible, high strength balloon lumens, said device comprising two or more such balloon lumens with substantially parallel longitudinal axes along at least said multi-lumen portion of said device wherein each of said balloon lumens shares a common, integrally-formed at least partially oriented wall portion with at least one adjacent balloon lumen along at least a section of their respective axial lengths and further wherein at least one of said planar wall portions defines a chord across a cross section of the cylindrical region.

31. Medical apparatus for use as or in combination with a balloon dilatation catheter made by the method of blow molding at least a portion of a multi-lumen, tubular element with a cylindrical interior, defined by a cylindrical wall portion, which is divided into two or more preform lumens by planar wall portions, said tubular element comprising orientable polymer, so as to expand said preform lumens and to thereby orient the polymer in at least one direction thereby forming a tubular segment comprising multiple expanded lumens of at least partially oriented polymer wherein said expanded lumens have the properties of being flexible and sufficiently thin-walled that they are readily inflatable under fluid pressure and readily collapsible under vacuum, said expanded lumens having integrally formed wall portions that are integral with another lumen and further wherein at least one of said planar wall portions defines a chord across a cross section of the cylindrical interior.

* * * * *